(12) United States Patent
Klein

(10) Patent No.: US 6,250,139 B1
(45) Date of Patent: Jun. 26, 2001

(54) PROCESS AND DEVICE FOR MEASURING MOISTURE IN POWDERS AND GRAINS AS WELL AS IN THE DRY MATTER OF LIQUIDS

(76) Inventor: André Klein, chemin du Grand Pin 9, Coraeau (CH), 1802

( * ) Notice: Subject to any disclaimer, the term of this patent is extended or adjusted under 35 U.S.C. 154(b) by 0 days.

(21) Appl. No.: 09/575,669

(22) Filed: Jun. 15, 2000

Related U.S. Application Data

(63) Continuation of application No. PCT/CH98/00544, filed on Dec. 18, 1998.

(30) Foreign Application Priority Data

Dec. 19, 1997 (CH) .................................................. 2922/97

(51) Int. Cl.$^7$ .............................. G01N 25/56; G01N 5/02
(52) U.S. Cl. ........................................ 73/76; 73/73; 73/74
(58) Field of Search ..................................... 73/73, 74, 76

(56) References Cited

U.S. PATENT DOCUMENTS 4,964,734    10/1990   Yoshida et al. ........................ 374/14

FOREIGN PATENT DOCUMENTS 0 344 465    6/1989   (EP) .

271 757    6/1989   (DE) .

OTHER PUBLICATIONS

A. Klein, "Causes of error of the Oven Method for Moisture Determination in Milk Powders," Abstract of Adresses at the International Dairy Federation 64$^{th}$ Annual meeting, 1980.

"AOAC Methods and Determination of Moisture," The Reference, AOAC International, vol. 17, No. 1, Jan. 1993.

*Primary Examiner*—Hezron Williams
*Assistant Examiner*—Dennis Loo
(74) *Attorney, Agent, or Firm*—Pennie & Edmonds LLP

(57) ABSTRACT

A method for measuring the moisture content in powders or other granular products or for measuring the dry matter of liquid products. The method includes the steps of placing the product on a scoop (8) and weighing it, then inserting the product on the scoop in a sealed glass tube (7), passing a dry gas stream to evacuate the product water content outside of the tube, such that the elimination step is carried out in a closed circuit independently of ambient air in the place where the product is being analyzed before measuring the drained product. The invention also relates to a measuring apparatus for implementing the method. This apparatus includes the sealed glass tube, a dry gas source, one or several sheaths or cells which house the glass tube and which are used for draining the product, gas flow regulators (2), one or several manometers (13), and a pump (14).

10 Claims, 3 Drawing Sheets

PROCESS AND DEVICE FOR MEASURING MOISTURE IN POWDERS AND GRAINS AS WELL AS IN THE DRY MATTER OF LIQUIDS

CROSS-REFERENCE TO RELATED APPLICATIONS

Continuity Data

This application is a continuation of the U.S. national stage designation of PCT/CH98/00544 of 18 Dec. 1998 now pending, the entire content of which is expressly incorporated herein by reference thereto;

STATEMENT REGARDING FEDERALLY SPONSORED RESEARCH

Not Applicable

Reference to a Microfiche Appendix

Not Applicable

Technical Field

This invention relates to a process as well as a moisture-measuring device for powders, grains and for the dry matter of liquid products. It therefore applies to numerous domains including food and agricultural products, such as milk, coffee, cocoa, tea, cereals and the like, as well as coal, paper, tobacco, and other products.

Background of the Invention

In order to establish water content, most international prescriptions FIL-IDF, ISO, AOAC, OICCC, IC, CCE including the Codex Alimentarius, recommend a gravimetric method whereby both the moisture and the dry matter of the sample are determined. Gravimetric analysis entails the drying of the product in an oven to constant weight, i.e., one where the difference in two successive weighings does not exceed 0.5 mg. The works carried out in rooms with controlled temperature and humidity revealed that results are significantly influenced by the prevailing climatic conditions. The humidity percentages of a same sample determined by the same analytical method can differ as much as 1.5%, according to where the analysis is made. For example, a sample exhibiting a 3% humidity content in Geneva (where the climatic conditions are 3 g water per $m^3$ air) may only yield a 2% humidity content in São Paulo (where the climatic conditions are 26 g water per $m^3$).

Brief Summary of the Invention

The invention relates to a process for measuring moisture in powders or grains, or for measuring dry matter of liquid products, wherein the sample and the dish are weighed together and then introduced into an air-tight glass tube through which a gas flows in order to remove any water produced by the sample, the water is thus eliminated in a closed circuit independently of climatic conditions. In this process, the loss in mass occurs firstly because of the individual heating of the product with the possibility of setting several different temperatures ranging from 40 to 150° C. and secondly because of the reduced pressure ranging from 10 mbar to atmospheric pressure. Also, the cooling of the dried product occurs within the tube under reduced pressure till ambient temperature is reached and by the fact the weighing is carried out only once the vacuum has been stopped and the atmospheric pressure recovered and the dish is extracted from the tube and is subsequently weighed with its cover on an analytical balance.

Advantageously, the gas used is nitrogen which first flows through a molecular sieve to remove any water traces before carrying the water produced by the sample towards the exterior of the tube, and that the reduced pressure within the tube created by the pump helps remove the last remaining traces of water in the product and in the tube. Preferably, the dry gas is introduced directly from a source within the whole device and that it is introduced through a medicinal needle with a lateral orifice to prevent it from being closed by the rubber of a septum at the extremity of the tube.

The invention also relates to a method for measuring the moisture content of powders or grains or for measuring the dry matter of liquid products, which comprises the steps of placing the product on a scoop and weighing it, inserting the product and scoop in a sealed glass tube, and passing a dry gas stream over the product to evacuate water content outside of the tube, with the water evacuation step is carried out in a closed circuit independently of ambient air in the place where the product is being analyzed before measuring the drained product.

Another embodiment of the invention relates to a measuring device for carrying out the method. The device includes a source of dry gas, one or several sheaths into which the glass tubes are fitted, a gas regulator, a manometer, a pump and by the fact that the glass tube is fitted at one end with a screw thread and a rubber septum which ensures that the device is air-tight when it is pierced by a needle and at the other end by a spherical rod equipped with a stopcock. Depending upon the products to be analyzed, the device advantageously permits individual heating and pressure conditions into each tube independently from one another. For example, when a 6 sheath device is utilized, six different temperatures may be set and six different products analyzed. The device preferably includes heating sleeves which wrap a steel sheath in which the glass tube is lodged.

Alternatively, a measuring apparatus for implementing the method includes the sealed glass tube, a dry gas source, one or several sheaths or cells which house the glass tube and which are used for draining the product, gas flow regulators, one or several manometers, and a pump.

BRIEF DESCRIPTION OF THE DRAWINGS

The following figures help understand the invention.

DETAILED DESCRIPTION OF THE PREFERRED EMBODIMENTS

Figure 1:
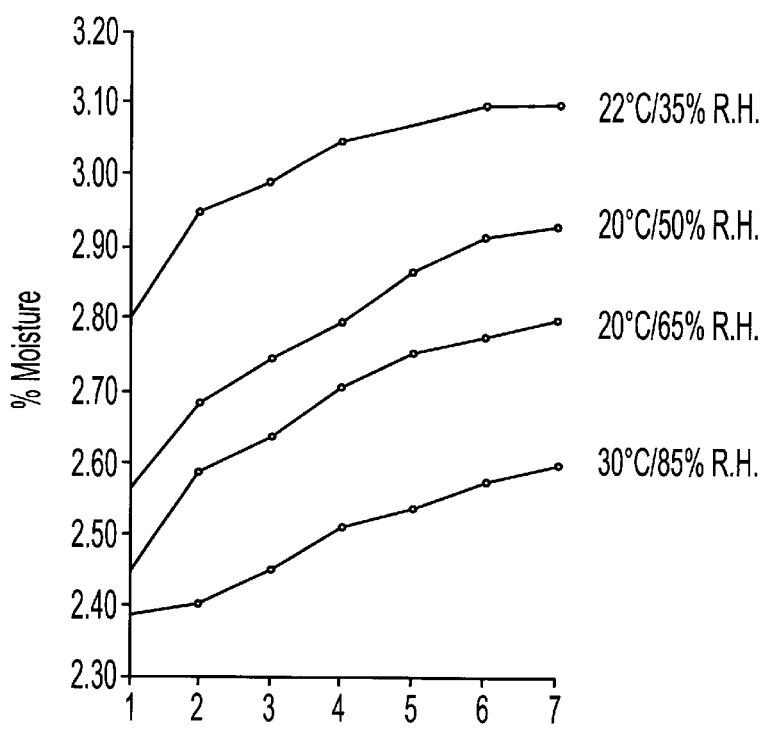
FIG. 1 is a graph which illustrates the influence of climatic conditions on prevailing international measuring methods.

The evolution of humidity percentage in powder milk according to various climates is plotted in FIG. 1. The results of this figure have been obtained using the prevailing recommended international methods. Other factors such as the quality of the analytical material (dishes), the uniformity of the temperature within the ovens, the quality of the desiccant, the hygroscopicity of the products may also influence results. What is outstanding is that the higher the absolute humidity of the air, the lower the humidity of the samples.

EP 0 344 465 relates to the determination of the humidity contained in coal, and states that the product is put into a dish in order to be weighed.

The nature of the samples determines the way in which they are prepared. Whereas powder milk is used as such, cheese, grains, and like products must be ground to a specific dimension.

Figure 2:
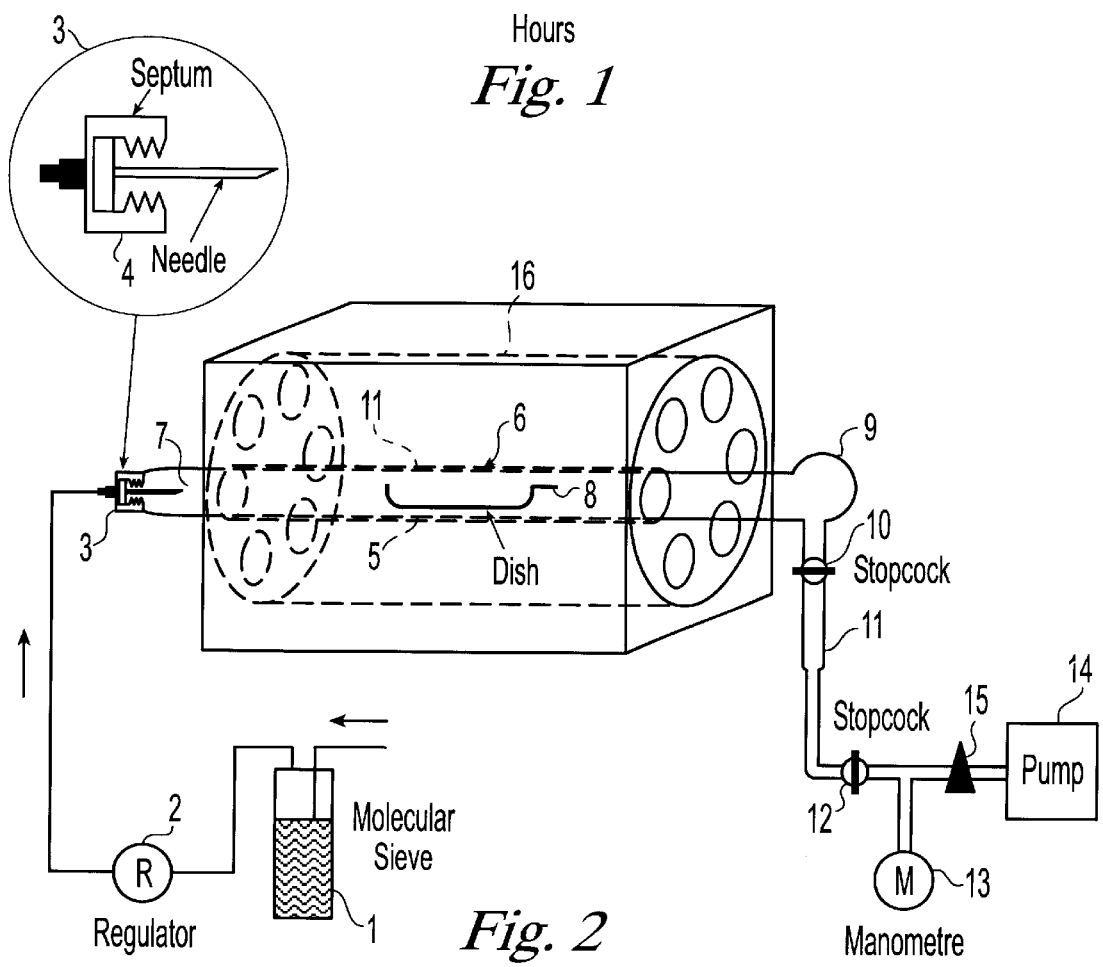
FIG. 2 illustrates various parts of an instrument according to the invention.
Figure 3:
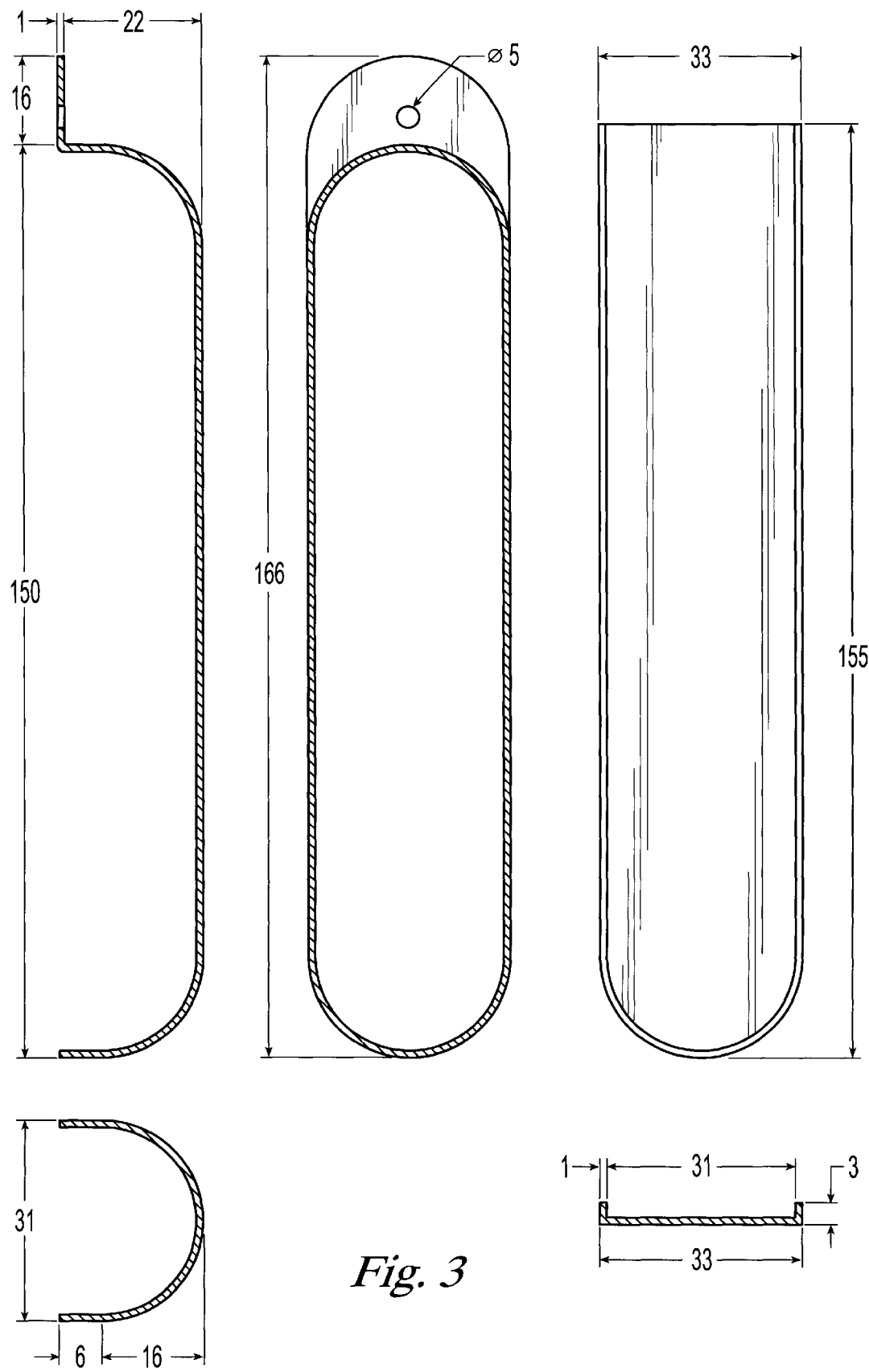
FIG. 3 illustrates the aluminum dish of the invention of FIG. 2.
Figure 4:
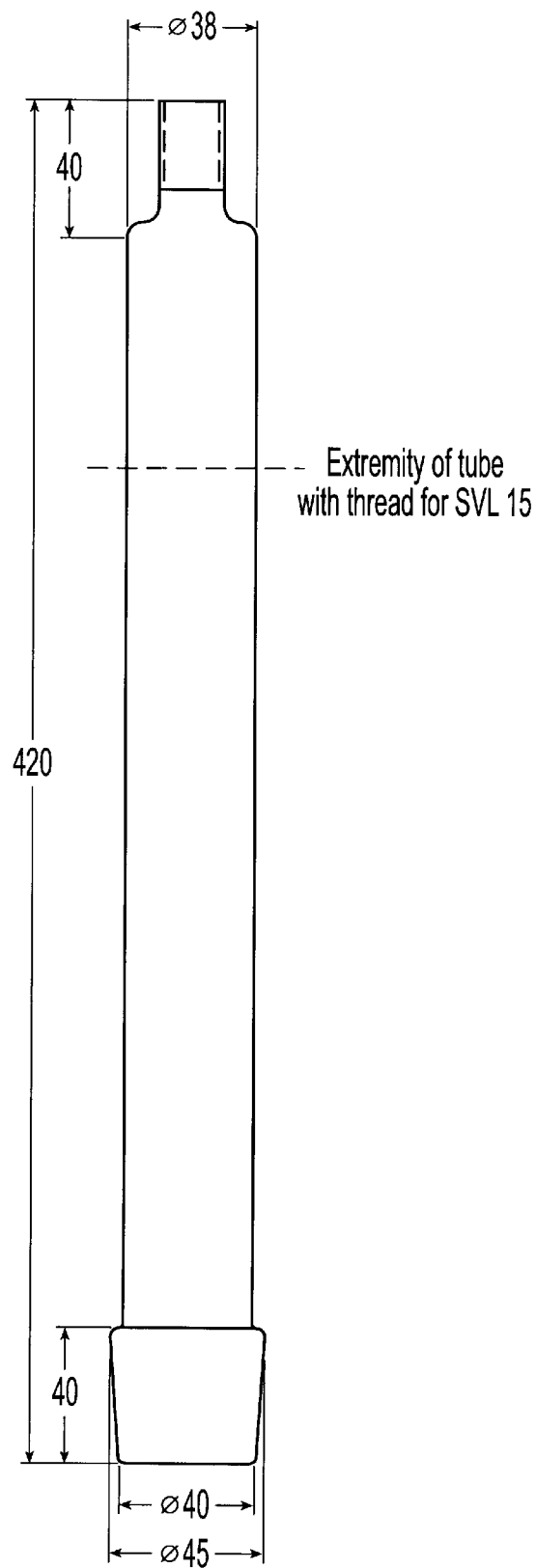
FIG. 4 illustrates the glass tube of the invention of FIG. 2.

After taring the dish (8) and its cover (FIGS. 2 and 3), 1–2 g of substance are accurately weighed (i.e., to the tenth of milligram). The substance and the dish (without cover) are introduced into a glass tube (7) fitted at one end with a cap (3) and rubber septum and at the other end with a spherical air-tight rod (9) equipped with a stopcock The glass tube (containing the dish and substance) is fitted into a steel sheath (5) which is itself inserted into a heating sleeve (6), the end of the tube with the cap (3) hits a needle (4) which pierces the septum allowing thus the gas to flow into the tube and to withdraw the water produced by the sample. The following elements are found at the other end of the glass tube: a stopcock (10) connected to a tube (11), it self connected to another a stopcock (12), then to a manometer (13), to a pressure regulator (15) and finally to the pump (14).

The gas is introduced into the tube (7) by means of a needle. Before entering the glass tube, the gas passes through both a molecular sieve (1) for any humidity traces to be removed and a flow rate regulator (2). Reduced pressure is obtained inside the tube by means of the pump (14).

The drying temperature as well as the vacuum inside the tube are adapted to each product. With a six sheath instrument, it is possible to set six different temperatures and therefore to work on six different products simultaneously. The difference in weight before and after the drying and the cooling, expressed in %, gives the loss in mass (humidity and/or dry matter) of the product.

All the different elements are assembled within one single enclosure (16).

DEPOSIT OF COMPUTER PROGRAM LISTINGS not applicable

What is claimed is:

1. A process for measuring moisture in powders or grains, or for measuring dry matter of liquid products, comprising:
   placing a sample of powder, grain or liquid product in a dish;
   weighing the sample and the dish a first time;
   introducing the sample and dish into an air-tight glass tube so that the sample is not exposed to atmospheric conditions, wherein the air-tight glass tube has a first end and a second end;
   maintaining a reduced pressure in the air-tight glass tube and heating the sample while flowing a dry gas through the air-tight glass tube to provide a dried sample;
   cooling the dried sample;
   weighing the sample and dish a second time; and
   determining the amount of water lost by the sample from the difference between the first weight of the sample and dish and the second weight of the sample and dish.

2. The process according to claim 1, wherein the sample is heated from 40 to 150° C. and the pressure is between 10 mbar and atmospheric pressure.

3. The process according to claim 1, wherein the dried sample is cooled within the air-tight glass tube under reduced pressure until ambient temperature is reached and further comprising allowing the pressure in the air-tight glass tube to reach atmospheric pressure; removing the dish from the tube and weighing the sample and dish the second time on an analytical balance.

4. The process according to claim 1, wherein the dry gas is nitrogen which flows through molecular sieves to remove traces of water before being introduced into the air-tight glass tube.

5. The process according to claim 1, wherein the first end of the air-tight glass tube is covered with a rubber septum and the dry gas is introduced through a medicinal needle that pierces the rubber septum, wherein the medicinal needle has a lateral orifice to prevent the needle from being closed by the rubber of the septum.

6. A method for measuring the moisture content of powders or grains or for measuring the dry matter of liquid products, comprising:
   placing the product on a scoop and weighing the scoop and product a first time;
   placing the product and scoop in a sealed glass tube that is not exposed to atmospheric conditions;
   passing a dry gas stream over the product to remove water from the product;
   removing the scoop and product from the sealed glass tube;
   weighing the scoop and product a second time; and
   determining the amount of water lost by the sample from the difference between the first weigh of the sample and scoop and the second weight of the sample and scoop.

7. A device for measuring moisture in powders or grains, or for measuring dry matter of liquid products, comprising one or more sheaths for accepting and surrounding one or more glass tubes containing a sample to be dried and heating the glass tubes, wherein the glass tubes have a first end with a screw thread and a rubber septum which ensures that the device is air-tight and a second end with a spherical rod equipped with a stopcock, wherein the first end of the glass tube is connected to a source of dry gas by a needle that pierces the rubber septum and the spherical rod is connected to a manometer and a pump for generating reduced pressure so that the dry gas flows over the sample.

8. The device of claim 7, wherein the temperature and pressure of each of the one or more glass tubes can be controlled independently.

9. The device of claim 7, wherein the sheaths are made of steel.

10. The device of claim 7, wherein six sheaths are present.

* * * * *

UNITED STATES PATENT AND TRADEMARK OFFICE
CERTIFICATE OF CORRECTION

PATENT NO. : 6,250,139 B1
DATED : June 26, 2001
INVENTOR(S) : A. Klein

It is certified that error appears in the above-identified patent and that said Letters Patent is hereby corrected as shown below:

<u>Column 4,</u>
Line 39, replace "weigh" with -- weight --.

Signed and Sealed this

Fifteenth Day of January, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 6,250,139 B1
DATED : June 26, 2001
INVENTOR(S) : André Klein

It is certified that error appears in the above-identified patent and that said Letters Patent is hereby corrected as shown below:

Title page,
Item [76], Inventor: replace "Coraeau" with -- Corseaux --.

Signed and Sealed this

Seventh Day of May, 2002

Attest:

JAMES E. ROGAN
*Attesting Officer*    *Director of the United States Patent and Trademark Office*